United States Patent [19]

Spadafora

[11] 4,405,650

[45] Sep. 20, 1983

[54] COMPRESSED YEAST PRODUCT AND PROCESS

[75] Inventor: Paul F. Spadafora, Lagrangeville, N.Y.

[73] Assignee: Nabisco Brands, Inc., Parsippany, N.J.

[21] Appl. No.: 286,723

[22] Filed: Jul. 27, 1981

[51] Int. Cl.³ ............................. A23J 1/18; A23J 3/00
[52] U.S. Cl. ...................................... 426/62; 426/426; 426/431; 426/454; 426/455; 426/656; 435/255; 435/256
[58] Field of Search ................. 426/62, 431, 426, 656, 426/454, 455; 435/255, 256

[56] References Cited

U.S. PATENT DOCUMENTS

| | | | |
|---|---|---|---|
| 2,868,649 | 1/1959 | Rosenqvist et al. | 426/62 |
| 2,947,668 | 8/1960 | Kuestler et al. | 426/62 |
| 3,150,980 | 9/1964 | Rosenqvist et al. | 426/62 |
| 3,681,199 | 8/1972 | Rokitansky | 426/62 |

*Primary Examiner*—Jeanette M. Hunter
*Attorney, Agent, or Firm*—Richard Kornutik

[57] ABSTRACT

Disclosed are an improved process for preparing compressed yeast and the product of that process. Prior to filtering yeast, it is conventional to contact the yeast with salt or other osmotically-active material to extract a portion of the intracellular water. Some solids are also withdrawn from the yeast cells; and, unless these are washed away prior to filtration, they tend to clog the filter medium. Our improvement concerns washing the yeast prior to filtration and results in increased filtration rates, increased filter medium life, and yeast of improved quality. The product yeast has improved color and plasticity and a lower salt content.

14 Claims, 1 Drawing Figure

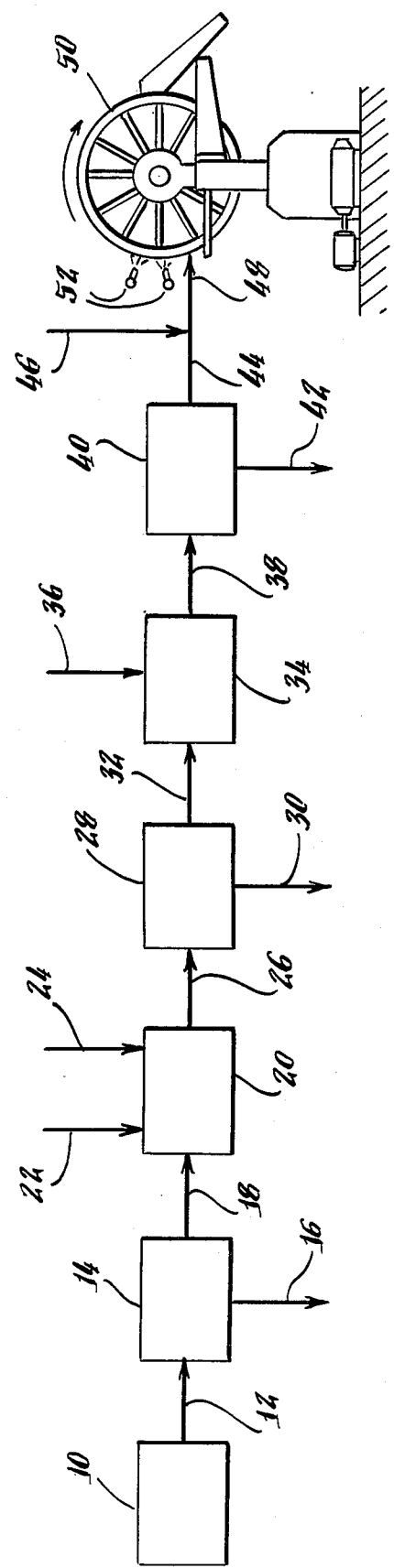

COMPRESSED YEAST PRODUCT AND PROCESS

BACKGROUND OF THE INVENTION

Present invention relates to an improved process for preparing compressed yeast. More particularly, it relates to a process which improves the filterability of the yeast and results in a product having improved properties.

The largest use for viable yeast is for baking purposes, and is supplied to bakeries and consumers in two principal forms, i.e., active dry and compressed. Compressed yeast typically contains about 30% yeast solids on a weight basis, whereas active dry yeast typically contains less than 10%, and generally from about 5 to about 8% moisture. Active dry yeast may be produced from a suitable compressed yeast by any of the several processes known in the art; for example, a process known as the "spaghetti process" which involves extruding compressed yeast in spaghetti form and drying it under controlled conditions on a moving belt.

Commercial yeast production typically entails propagation in a plurality of stages to attain the high degree of purity required for baking purposes. Typically, propagation starts with seed stages and finishes with growing in fermentors of commercial scale. The yeast is grown under aerobic conditions by the addition of large volumes of air to the growth medium. Carbohydrates and nitrogen sources are continuously incorporated into the yeast mash in the last stages of propagation. The temperature of the growth media is maintained in the range where optimum growth of the yeast occurs.

After propagation of the yeast, the yeast is separated from the other constituents of the growth media such as by centrifugation to produce a cream yeast which typically contains about 18% solids. The cream yeast is then washed by redispersing it in water and reconcentrating it to form a purified cream yeast suspension.

In order to produce a commercial compressed yeast product, a cream yeast suspension is subjected to filtration in order to increase the solids content and to reduce the plasticity to improve shaping and forming of the yeast in subsequent stages. Traditionally, the filtration equipment used in the industry includes filter presses or suction filters, with rotary vacuum filters being particularly preferred. Filter presses require the application of high pressures, on the order of 12 atmospheres or more, to force the liquid phase of the yeast suspension through a filtering medium which usually consists of a canvas or fiber cloth. The suction filters function by creating an area of reduced pressure on one side of the filtering medium, usually by the use of a vacuum pump, which causes the liquid phase of the yeast suspension to be drawn through the filtering medium. Commercially, the maximum practical pressure differential that can be obtained on rotary vacuum filters is less than one atmosphere.

In order to increase the solids content of the compressed yeast, Kuestler et al in U.S. Pat. No. 2,947,668, suggest adding an osmotically-active compound, such as sodium chloride to the yeast cream prior to filtration to withdraw intracellular water from the individual yeast cells. The cream yeast suspension is allowed to remain in contact with the osmotically-active compound until the exudation of water due to the difference in osmotic pressure between the intracellular water and the extracellular water is completed. This usually requires several minutes, after which period of time the cream yeast suspension is subjected to vacuum filtration. To reduce the level of osmotically-active compound such as salt in the final product, while not permitting rehydration of the individual yeast cells, the yeast is washed while on the rotary vacuum filter drum. This enables displacement of the osmotically-active material from the extracellular water in an extremely short period of time without permitting the wash water to remain in contact with the yeast cells long enough for reabsorption of any significant amount of water. The contact is disclosed to be from about 0.5 to about 1.5 seconds, in many cases, depending upon the thickness of the yeast layer.

The remainder of the process disclosed by Kuestler et al is then similar to the prior art which existed at that time. The principal difference being that where the vacuum filtration is capable of withdrawing sufficient extracellular water to achieve a slightly less than adequate degree of firmness, at least a portion of the remaining extracellular water is reabsorbed into the individual yeast cells after filtration to result in increased firmness and decreased plasticity. The patent emphasizes, however, that to achieve this desired result, the step of washing the yeast free of the osmotically-active compound must be done extremely rapidly so that a difference in osmotic pressure between intracellular water and the extracellular water remains after filtration. If contact with the washing water is maintained for greater than this minimal time, extracellular water will be taken into the individual yeast cells, driven by the osmotic pressure differential, prior to completion of filtration, and there will be no osmotic pressure differential left to further draw in extracellular water to provide the desired increase in firmness.

It has been my observation that the addition of salt or other osmotically-active compounds in the concentrations prescribed by the Keustler et al patent causes not only water to be removed from the interior of the individual yeast cells, but also causes the release of soluble solids from the interior of the cells and other solids loosely held to the exterior of the cells. These substances tend to collect within the interstices of the filtering medium and interfere with filtering efficiency.

In one particular commercial yeast filtering operation employing rotary vacuum filters, the filtering medium is made up of a layer of starch particles deposited on a cloth or metal mesh on the surface of vacuum drum. The yeast is applied to the filtering medium on the surface of the drum, and the extracellular water is drawn through the filtering medium towards the interior of the drum to the extent possible due to the applied pressure differential. The resulting filter cake which comprises yeast having a solids content of 30% or greater, is normally removed from the drum by means of a cutoff knife. In normal commercial practice, the knife will be intermittently or continuously advanced towards the surface of the drum to remove the yeast cake and the very top layer of the starch-filtering medium. This top layer must be continuously removed in very fine cuts because it becomes plugged by the solid substances which are present in the liquid phase of the yeast suspension.

The amount of extracellular solids in a yeast suspension varies with many factors; however, one of the prime factors responsible for high levels is the addition of salt or other osmotically-active material to the cream yeast suspension. Thus, the achievement of the desired plasticity according to the Kuestler et al patent also releases solid substances which interfere with the efficiency of filtration. These interfering substances, when present in large quantities, tend to bind the filtering medium to a point at which the desired low moisture content for the filter cake cannot be obtained without the knife being advanced so rapidly into the starch coating that the amount of starch being cut off with the product is brought to an unacceptably high level. This requires more frequent replacement of the starch layer on the filter and also greatly reduces the feed rate of cream yeast to the filter and subsequent production of compressed yeast.

Accordingly, it would be desirable to have a process which retained the benefits of improved plasticity by treatment before filtration with an osmotically-active agent, while improving the rate of filtration and the life of the filtering medium. Moreover, it would be desirable to provide a process which improved the ultimate quality of the compressed yeast produced.

SUMMARY OF THE INVENTION

It is an object of the present invention to provide a simple and effective process to improve the filtering characteristics of yeast.

It is another and more specific object of the present invention to improve the filtering characteristics of yeast by a simple and effective process which reduces the deposit of interfering materials in the open lattice of the filtering medium.

It is a yet further and more specific object of the present invention to provide a simple and effective process for improving the filtering characteristics of yeast which, by reducing the deposit of interfering materials in the open lattice of the filtering medium, improves the rate of filtration and decreases the maintenance required to maintain the filtering medium in serviceable condition.

These and other objects are accomplished according to the present invention which provides an improved process for filtering yeast and the product of that process. In its broad aspects, the process comprises: contacting a yeast suspension with a sufficient amount of an osmotically-active material to withdraw water from the interior of individual yeast cells, maintaining contact for a period of time effective to withdraw water and soluble solids which interfere with filtration from the interior of individual yeast cells, dispersing the yeast suspension in addition water, removing water containing dissolved osmotically-active material and soluble solids freed from the yeast cells during contact, and then filtering the yeast.

BRIEF DESCRIPTION OF THE DRAWING

The invention will be better understood and its advantages will become more apparent from the following description, especially when read in light of the attached drawing, wherein:

the FIGURE is a schematic representation of a preferred processing flow diagram according to the present invention.

DETAILED DESCRIPTION

The process of the invention improves the production of compressed yeast essentially by providing an improved process for filtering the yeast. The process of the invention is particularly suitable for preparing baker's yeast, but is also suitable for preparing other types of yeast, both as active dry and compressed. The species of yeast used for baking purposes is generally *Saccharomyces Cerevisiae*. There are many strains of yeast which are included within the species and the particular strain used depends upon many factors, such as the desired form of the yeast.

Strains of bakers' yeast can be generally grouped into broad categories when classified according to the bios response procedure published by Schultz and Atkin in *Archives of Biochemistry*, Volume 14, Page 369 (August 1949). One group is classified as bios No. 236. Yeast in this group is generally used when it is desired to produce compressed yeast. Compressed yeast is generally formed into bricks of suitable size and contains about 70% moisture. Another group is classified as bios No. 23, and is typically employed when an active dry yeast is to be produced. Although yeast of the bios No. 23 group can be propagated to higher yields, and is hardier and more stable than yeast of the bios No. 236 group, compressed yeast of the latter group is preferred by commercial bakers because of its superior leavening activity.

Active dry yeast typically contains less than 10% moisture, and generally from about 5 to 8% moisture. Yeast of the bios No. 23 group is usually selected for the production of active dry yeast because its properties of being more hardy and metabolically stable than bios No. 236, enables it to be dried to lower moisture levels with minimum loss of its initial leavening activity. In some instances, yeast of the bios No. 236 group can be used to prepare an active dry yeast product.

The propagation of the yeast, whether of the bios No. 23 group or the bios No. 236 group, and also regardless of the particular end use as active dry or compressed yeast, is generally carried out in a stage-wise process to form a yeast mash. The yeast mash will then be separated into a cream yeast portion which comprises an aqueous suspension of yeast, and a beer portion. The cream yeast portion is then subjected to filtration to prepare compressed yeast. The compressed yeast can be employed as is, or it can be subjected to further processing including drying to produce an active dry yeast. Thus, the process of the present invention which improves the production of compressed yeast, is also applicable to the production of the compressed yeast intermediately employed in the production of active dry yeast.

The production of the initial mash which can then be purified and filtered in improved manner according to the present invention is done in conventional manner. A typical commercial practice for the propagation of yeast and the preparation of a yeast mash is described by Frederick W. Nordsiek in *Food Engineering*, McGraw-Hill Publishing Company, New York, NY, May 1951. Also pertinent are the teachings of U.S. Pat. No. 3,617,306 to Pomper et al and U.S. Pat. No. 4,008,335 to Akerman et al. The teachings of these references are hereby incorporated by reference in their entireties for their discussion of the production of suitable yeast mashes.

The FIGURE shows a preferred process flow diagram for producing a compressed yeast according to the invention. According to this arrangement, a yeast mash is transferred from a fermentor 10 via line 12 to a centrifuge 14 wherein it is separated into an aqueous yeast suspension referred to as a yeast cream and an aqueous ferment portion referred to as a beer. The beer is removed from the process via line 16 and subjected to independent processing as known in the art. The yeast cream is transferred via line 18 to tank 20 wherein it is contacted with a sufficient amount of an osmotically-active material, added via line 22, to withdraw water from the interior of individual yeast cells.

As referred to in the art, yeast creams typically contain from about 4 to about 6 pounds of yeast per gallon, the weight of the yeast being determined on the basis of a 30% yeast solids content. Yeast suspensions other than yeast creams fitting this definition can be effectively processed according to the invention; however, the use of yeast creams according to this definition are preferred commercially.

Among the suitable osmotically-active materials are electrolytes and non-electrolytes which are suitably soluble in water at the intended processing conditions, and which have a combination of desirably low molecular weight and other physical properties which make them effective at practical concentrations for creating an osmotic pressure differential between the intracellular yeast water and the extracellular water to draw water from the individual yeast cells. Further, the osmotically-active materials should be non-toxic and should not otherwise adversely affect the color or characteristics of the product yeast. In this regard, the teachings of U.S. Pat. No. 2,947,668 to Kuestler et al are specifically incorporated by reference. Preferred osmotically-active materials are water-soluble substances selected from the group consisting of: sodium salts, potassium salts, ammonium salts, calcium salts, magnesium salts, aluminum salts, alcohols, organic nitrogen containing compounds, carbohydrates not fermentable by yeast, and combinations of these. Sodium chloride is particularly preferred because of its strong osmotic effect, its economy, and its overall compatibility with the process and end-product uses.

The yeast is maintained in contact with the solution of the osmotically-active material for a period of time effective to withdraw water and soluble solids which interfere with filtration from the interior of individual yeast cells. While it has not been specifically desired to withdraw the solids from the interior of the yeast cells, it has been noted that this is the natural result of the osmotic action where the contact is maintained for a period of time effective to withdraw a sufficient amount of water from within the cells to obtain a significant improvement in yeast plasticity. The contact further frees a substantial quantity of solids which are loosely adhered to the exterior of the cell walls. We have found that the soluble solids which are withdrawn from the interior of the yeast cells and those which are freed from the exterior thereof, tend to collect within the interstices of the filtering medium during filtration unless removed prior to filtration.

Where sodium chloride is employed as the osmotically-active material, it has been found that amounts of from about 0.1 to about 10% based upon the weight of the yeast suspension are effective. More preferred levels, when employing a yeast cream containing from about 4 to about 6 lbs. of 30% solids yeast per gallon, are within the range of from about 1 to 5% based on the weight of the yeast suspension. The time of contact will depend upon the type of osmotically-active material, the concentration of the osmotically-active material, and the temperature of contact. Typically, contact times of from about 1 to about 30 minutes will be effective at the preferred concentrations at ambient temperature. More preferably, when employing sodium chloride as the osmotically-active material in the preferred concentration to contact a yeast cream at the preferred concentration, the contact time will be within the range of from about 5 to about 20 minutes.

After maintaining contact for the desired period of time, the yeast suspension in tank 20 is washed by introducing water via line 24 and then removing the water containing dissolved osmotically-active material and soluble solids freed from the yeast cells during contact. The amount of water employed will vary widely with the desired degree of extraction of osmotically-active material and other soluble solids, the number of washing steps which can be economically employed, and the choice as to whether the process is to be continuous or batch wise. Typically, the water employed to disperse the yeast after contacting the yeast with the osmotically-active material, will be employed in an amount of from about 0.1 to about 10 volumes of water per volume of yeast suspension. Preferably, in the exemplary case where sodium chloride is employed at the preferred level as the osmotically-active material to contact a yeast cream at the preferred solids concentration, and where a single washing stage is employed, the water used to disperse the yeast directly following this initial contact step will be employed in an amount of from about 1 to about 5 volumes of water per volume of yeast suspension. Most preferably, the amount of water employed will be approximately that necessary to bring the yeast solids concentration to approximately that present in the initial mash as it was present in fermentor 10.

Following the addition of wash water to the appropriate volume via line 24, the resulting aqueous yeast suspension is passed from vessel 20 via line 26 to a separatory device 28. In the separatory device 28, water containing dissolved osmotically-active material and soluble solids freed from the yeast cells during contact is removed via line 30. The separatory device 28 can be either a settling tank wherein the suspension supplied via line 26 is permitted to settle with the water being decanted in conventional fashion, or it can be a centrifuge capable of batch or continuous operation. Preferably, the centrifuge will be of the nozzel type, such as a Westphalia or Alpha Laval. In the case of removing the water by centrifugation, the conditions are preferably selected to be effective to reduce the overall water content to less than about 88%. In the case of settling and decantation, the conditions are preferably selected to be effective to reduce the overall water content to less than about 92%.

The yeast suspension remaining after removal of the water is passed from the separatory device 28 to a second washing stage via line 32. This second washing stage is illustrated to take place within vessel 34 wherein the suspension of yeast is redispersed in water added via line 36. The water will be added in an amount within the range employed in the first washing stage. Preferably, the amount of water will be about the same as that previously added.

From the second washing stage, the resulting diluted yeast suspension is passed via line 38 to a separatory device 40 wherein the suspension is reconcentrated by removal of an aqueous extract via line 42 and a purified yeast cream via line 44. Separatory device 40 can be of the same type employed for device 28, or it can be different. The type of device and the conditions for operating should, however, be selected to achieve a moisture content within the purified yeast cream to less than about 88% and preferably within the range of from about 81 to about 85%. The moisture should be closely controlled in this stage because it is passed from here for final processing by filtration to form a compressed yeast product.

The purified yeast cream is withdrawn from the separatory device 40 via line 44 and is preferably contacted with an osmotically-active material in an amount effective to withdraw water from the interior of individual yeast cells. This processing stage, unlike the earlier stage of contacting the yeast with an osmotically-active material, is for the purposes disclosed by Kuestler et al in U.S. Pat. No. 2,947,668. The withdrawal of intracellular water directly prior to filtration enables the filtration step to reduce the overall water content of the yeast to a lower level. This is possible because, as explained by Kuestler et al, the pressure differential applied during filtration will be capable of achieving only a given lower level of extracellular water, and that amount of water is fairly well limited by the processing conditions; however, after filtration an amount of the extracellular water can be reabsorbed by the individual yeast cells where the osmotic pressure of the extracellular water is decreased to a level below that of the intracellular water.

To achieve the preferred reduced extracellular water content and the preferred reduced plasticity, the purified yeast cream containing the osmotically-active material added via line 46 is passed via line 48 to a suitable filtering device 50 whereon it is immediately, briefly contacted with a spray of wash water via lines 52 which is sprayed onto the exterior of the yeast on the surface of filter 50 and is immediately drawn through the yeast by an applied vacuum to carry the majority of the osmotically-active material from the yeast. In this manner, as disclosed by Kuestler et al, the osmotic pressure of the extracellular water is reduced to a level which upon setting drives water from the exterior of the cells into the interior thereof to reduce the plasticity of the compressed yeast product.

Typically, the compressed yeast will have a moisture content of less than about 71%, and preferably the moisture content will be within the range of from about 64 to about 68%. While the level of osmotically-active material added during this filtration stage can be at about the same levels as previously disclosed with regard to the first contact step in vessel 20, it is an advantage of the present invention that one can employ a lower level and yet obtain similar benefits with regard to moisture content and plasticity as would be achieved with the use of the higher level but without the first contact stage. It is also an advantage of the present invention that the first contact with the osmotically-active material in vessel 20 withdraws a large amount of color bodies which, by virtue of their removal from the system, enables the production of a yeast product having a lighter, more pleasing color. In addition to these improvements in the product resulting from the process, the efficiency of the filtration process itself is improved because solid materials which would normally interfere with filtration by plugging the filter medium are removed in the washing step subsequent to the initial contact with the osmotically-active material. The removal of these interfering solid substances increases the rate of filtration and the useful life of the medium between cleaning operations.

While any filtering medium and device known to the art can be employed, filter presses and rotary vacuum filtering devices are preferred. With rotary vacuum filters, the commercial practice has been to use a filtering medium of starch particles deposited on a cloth or metal mesh on the surface of the drum. The filter cake is normally removed from the drum by means of a cut-off knife. In normal commercial practice, the knife either continuously or intermittently advances to remove the yeast cake, and is also used to remove the very top layer of the filtering medium. This top layer becomes plugged by extracellular substances which are present in the liquid phase of the yeast suspension. The amount of extracellular material varies with many factors; however, one of the prime factors responsible for high levels is the addition of salt or other osmotic material to the cream. According to the teachings of the above-identified Kuestler et al patent, the addition of salt or other osmotically-active material prior to filtration is necessary to obtain a desirably high solids level with good plasticity. However, the addition of salt or other compound in the prescribed concentration not only causes water to be removed from the cell, but other interfering compounds are also released from the interior of the cell, as well as some loosely-bound materials which are held on the exterior of the cell wall. These interfering substances, when present in large quantities, tend to bind the filtering medium to a point whereby the low moisture cannot be obtained without advancing the knife into the starch so rapidly that the amount of starch pre-coat material being cut off with the product is brought to an unacceptably high level. This further drastically reduces productivity because it necessitates a lower feed rate of yeast suspension to the filter and requires extra downtime for recoating the filter medium.

According to the present invention, it is possible to obtain the benefits of the teachings of the above-identified Kuestler et al patent while improving the efficiency of the filtration process and also improving the final quality of the compressed yeast product. In the initial contact of the yeast suspension with the osmotically-active material as described above, water and interfering solid materials are withdrawn and freed from individual yeast cells to enter the extracellular water. These materials are then in large part removed by one or more washing stages which also permit rehydration of the individual yeast cells to substantially their original moisture contents. Thus, the initial step of contacting the yeast suspension with the osmotically-active material according to the present invention is distinct from that of the above identified Kuestler et al patent in that the subsequent washing stage is not of such limited duration that the yeast cells are held to their resulting lower moisture contents. On the contrary, the yeast cells are substantially fully rehydrated, but substances which would normally interfere with the filtration process are effectively removed prior to filtration. Where it is then desired to achieve the disclosed advantages of the above-identified Kuestler et al patent, a second contacting step is employed.

The improvement of the present invention is manifested by a number of features. The present invention provides improved solids content with lower extracellular water in keeping with the advantages of the Kuestler et al patent. Moreover, the present invention reduces the deposit of interfering materials in the open lattice of the filtering medium, thereby reducing the need to wash the cloth medium in the case of a filter press or to reduce the cut into the starch medium in the case of a rotary vacuum filter. Additionally, the concentration of the salt or other osmotically-active material added just prior to filtration to obtain the desired compressed yeast moisture can be lowered from that conventionally employed, thereby reducing the residual salt level with the same efficiency of the wash step.

The following examples are presented for the purpose of further illustrating and explaining the present invention and are not to be taken as limiting in any regard. Unless otherwise indicated, all parts and percentages are by weight.

EXAMPLE 1

The process of the present invention, wherein a yeast suspension is contacted with an osmotically-active material and then washed prior to the filtration stage, is compared on a commercial scale to a control process wherein a yeast suspension is washed prior to filtration but without the addition of the osmotically-active material.

A commercial yeast fermentation is conducted and the resulting mash is divided into equal volumes which are then separately treated.

The control test employs 30,000 gallons of yeast containing 1 pound of 30% solids yeast per gallon. This portion is then fed to a Westphalia centrifuge wherein it is concentrated by removal of the beer to obtain 5,500 gallons of a yeast cream containing 5.45 pounds of 30% solids yeast per gallon. This yeast cream is then rediluted with wash water to a volume of 22,000 gallons and is then again centrifuged to a volume of 5,500 gallons. A second washing step with the same degree of dilution and centrifuging to the same final yeast solids concentration is then effected. Salt is added to the yeast cream at a level of 3.1% based on the weight of the cream. The resulting yeast cream is held for 10 minutes and is then fed at a rate of 9 gallons per minute to an AMETEK rotary filter device having a starch coated filtering medium.

The second half of the mash is then treated in accordance with the present invention by concentrating it in the same manner as the control to a yeast cream having a volume of 5,500 gallons at 5.45 pounds of 30% solids yeast per gallon. To this yeast cream, 3.4% salt, based upon the weight of the sodium chloride to the weight of the cream, is admixed. The sodium chloride readily goes into solution in the yeast cream which is at a temperature of about 80° F. and is maintained in contact therewith for a period of about 10 minutes. After this period of contact, the yeast cream is diluted with wash water to a volume of 22,000 gallons and is then centrifuged in the manner of the control to a volume of 5,500 gallons. This purified yeast cream is then rewashed and centrifuged again in the same manner as the control. The resulting yeast cream is then filtered on the same device and at the same rate as for the control, except that the amount of salt added directly prior to filtration is reduced from a level of 2.5 to 1.7%.

The portion processed according to the invention gives a dry, firm yeast cake which is lighter in color, at a lower salt addition level in the mix tank, and also contains a lower residual salt level than the product prepared from the control half of the mash. Long-term testing further indicates that when the mashes are processed in accordance with the invention, the starch coatings on the rotary vacuum filter last between 16 and 20 hours before replacement is necessary, whereas where no salt washing step is employed, the starch coatings last only from about 8 to about 16 hours. The yeast products from both portions of the mash are also tested for leavening activity in both straight dough and high sugar content dough procedures and indicate that no signficant difference in leavening activity appears between the samples. The further results of the testing are summarized as follows:

|  | Control | Invention |
|---|---|---|
| Salt addition in mix tank (Weight % based on weight of yeast suspension) | 3.1 | 2.2 |
| filter cake moisture (weight %) | 62.3 | 64.0 |
| Residual salt in cake (weight %) | 0.14 | 0.12 |
| Color of product (1 = lightest; 5 = darkest) | 4 | 2 |
| Plasticity of the cake (based on feel and bending before break; 1 = Firmest, 3 = Average, 5 = Gummy). | 4 | 2 |

EXAMPLE 2

This example compares the process of the present invention to a number of controls on a laboratory scale.

Filters for the test are prepared by casting a starch solution on the surface of a 140 cm diameter Buchner Funnell using No. 4 Filter Paper. The starch solution is prepared by first preparing a standard starch solution containing 125 gms of potato starch in 425 ml of deionized water. After 2 minutes, 50 ml of the standard starch solution is then diluted to 100 ml with additional deionized water. The 100 ml of diluted starch solution is then cast upon the 140 cm diameter Buchner Funnel using No. 4 Filter Paper to form the filter bed employed in the following tests.

A portion of yeast cream is subjected to a step wherein sodium chloride is contacted with the cream and then washed therefrom prior to filtration in accordance with the present invention. This procedure is accomplished according to the following steps:

(a) A quantity of 700 gms of cream at about 17 Blg, are mixed with 28 gms of salt and held for 15 minutes.

(b) The resulting cream mixture is then centrifuged in solid bowl International centrifuge (Model IEC Clinical) at setting of 5, and held in centrifuge for 10 minutes after all cream is in.

(c) All of cake is removed from the bowl brought up to the original volume with water, and mixed well.

(d) Step (b) is repeated.

(e) The resulting cake is removed from the bowl and weighed. The cake is then made up to 6.2 pounds of cream yeast per gallon (0.744 gms/ml)

Example: Centrifuge cake = 250 gms at 75% moisture $$\frac{250 \text{ gms}}{.744 \text{ gms/ml}} \times \frac{.25}{.30} = 250 \text{ gms} \times 1.12 = 280 \text{ ml}$$

(f) A quantity of 100 ml of cream from step (e) is filtered, using the standard starch bed prepared above at an applied vacuum of 419 mm of mercury. Times are observed with stop watch and recorded for: time for appearance of the first dry spot (18 mm in diameter), time until the complete top appears dry, and time it takes to get to one drop every two seconds.

(g) Filtrates are collected and compared for color.

(h) Filter cakes are collected and compared for color.

Three other test batches are prepared in similar manner but are varied in accordance with the sample treatments indicated in the following table:

| Sample Treatment | Water Washed Control | 2 Salt Wash | 3 Reg. Control | 4 Starch Treated |
|---|---|---|---|---|
| Add 4% Salt | No | Yes | No | No |
| Centrifuge | Yes | Yes | No | No |
| Wash | Yes | Yes | No | No |
| Centrifuge | Yes | Yes | No | No |
| Bring up to vol | Yes | Yes | No | No |
| Add .5% starch | No | No | No | Yes |
| Add 3% salt | Yes | Yes | Yes | Yes |
| Filter | Yes | Yes | Yes | Yes |

The results of these tests are as follows:

| | Water Washed Control | 2 Salt Wash | 3 Reg. Control | 4 Starch Treated |
|---|---|---|---|---|
| Time of 1st Dry Spot on Filter Cake (sec) | 65 | 60 | 100 | 95 |
| Time to Complete Dry Top on Filter Cake (sec) | 135 | 125 | 165 | 150 |
| Time to One Drop Every 2 Seconds (sec) | 195 | 175 | 215 | 215 |
| Vacuum at End (mm Hg) | 419 | 419 | 445 | 419 |
| Color of Cake (1 = lightest, 5 = darkest) | 3 | 1 | 2 | 4 |
| Color of Filtrate (1 = lightest, 5 = darkest) | 2 | 1 | 4 | 3 |

The above description is for the purpose of teaching the person of ordinary skill in the art how to practice the present invention and is not intended to detail all of its obvious modifications and variations which will become apparent to the skilled worker upon reading. It is intended, however, to include all such modifications and variations within the scope of the present invention which is defined by the following claims.

What is claimed is:

1. A process for preparing compressed yeast, which comprises:
   contacting a first stage yeast suspension with a sufficient amount of an osmotically-active material to withdraw water from the interior of individual yeast cells, maintaining contact for a period of time effective to withdraw water and soluble solids which interfere with filtration from the interior of individual yeast cells, dispersing the first stage yeast suspension in additional water, removing a portion of the water containing dissolved osmotically-active material and soluble solids freed from the yeast cells during contact to prepare a second stage yeast suspension;
   then contacting the second stage yeast suspension with an osmotically-active material at a concentration lower than that employed to contact the first stage suspension but sufficient to withdraw water from the interior of individual yeast cells; and then filtering the yeast.

2. A process according to claim 1 wherein the first and second suspensions are contacted with an osmotically-active material in an amount of from about 0.1 to about 10% based on the weight of the yeast suspension.

3. A process according to claim 2 wherein the first and second yeast suspensions comprise cream yeasts containing from about 4 to about 6 pounds of 30% solids yeast per gallon.

4. A process according to claim 1 wherein the water employed to disperse the first yeast suspension after contacting the first yeast suspension with the osmotically-active material, is employed in an amount of from about 0.1 to about 10 volumes of water per volume of yeast suspension.

5. A process according to claim 4 wherein the water added to disperse the first yeast suspension, and containing dissolved osmotically-active material and soluble solids freed from the yeast cells, is removed by centrifugation under conditions effective to reduce the overall water content to less than about 88%.

6. A process according to claim 4 wherein the water added to disperse the first yeast suspension, and containing dissolved osmotically-active material and soluble solids freed from the yeast cells, is removed by settling and decantation under conditions effective to reduce the overall water content to less than about 92%.

7. A process according to claim 1 wherein the osmotically-active material is a water soluble material selected from the group consisting of: sodium salts, potassium salts, ammonium salts, calcium salts, magnesium salts, aluminum salts, alcohols, organic nitrogen-containing compounds, carbohydrates not fermentable by yeast, and combinations of these.

8. A process according to claim 7 wherein the osmotically-active material comprises sodium chloride.

9. A process according to claim 7 wherein the sodium chloride concentration is within the range of from about 1 to about 5% based on the weight of the yeast suspension.

10. A process according to claim 9 wherein the water employed to disperse the yeast after the initial step of contacting the first yeast suspension with the sodium chloride, is employed in an amount of from about 0.1 to about 10 volumes of water per volume of yeast suspension.

11. A process according to claim 10 wherein the water is employed in an amount of from about 1 to about 5 volumes of water per volume of yeast suspension.

12. A process according to claim 11 wherein the water added to disperse the first yeast suspension directly following the initial step of contacting the first yeast suspension with sodium chloride, and containing dissolved sodium chloride and soluble solids freed from the yeast cells, is removed by centrifugation under conditions effective to reduce the overall water content to less than about 88%.

13. A process according to claim 11 wherein the water added to disperse the first yeast suspension directly following the initial step of contacting the first yeast suspension with sodium chloride, and containing dissolved sodium chloride and soluble solids freed from the yeast cells, is removed by settling and decantation under conditions effective to reduce the overall water content to less than about 92%.

14. A product produced by the process of either of claims 1 or 13.

* * * * *